United States Patent
Izu et al.

(10) Patent No.: US 8,647,679 B2
(45) Date of Patent: Feb. 11, 2014

(54) CORE-SHELL TYPE ZINC OXIDE MICROPARTICLE OR DISPERSION CONTAINING THE MICROPARTICLE, AND PRODUCTION PROCESS AND USE OF THE MICROPARTICLE OR THE DISPERSION

(75) Inventors: Noriya Izu, Aichi (JP); Ichiro Matsubara, Aichi (JP); Toshio Itoh, Aichi (JP); Woosuck Shin, Aichi (JP); Maiko Nishibori, Aichi (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 285 days.

(21) Appl. No.: 12/865,464

(22) PCT Filed: Feb. 6, 2009

(86) PCT No.: PCT/JP2009/052087
§ 371 (c)(1),
(2), (4) Date: Aug. 11, 2010

(87) PCT Pub. No.: WO2009/099201
PCT Pub. Date: Aug. 13, 2009

(65) Prior Publication Data
US 2010/0330008 A1 Dec. 30, 2010

(30) Foreign Application Priority Data
Feb. 7, 2008 (JP) ................................. 2008-027346

(51) Int. Cl.
| A61K 33/32 | (2006.01) |
| A61K 8/00 | (2006.01) |
| A61K 9/00 | (2006.01) |
| A01N 25/26 | (2006.01) |
| A01N 55/02 | (2006.01) |

(52) U.S. Cl.
USPC ............. 424/641; 424/59; 424/400; 424/421; 514/494

(58) Field of Classification Search
USPC ...................... 424/641, 59, 400, 421; 514/494
See application file for complete search history.

(56) References Cited

U.S. PATENT DOCUMENTS

| 3,544,500 | A * | 12/1970 | Moody et al. ............ 428/402.24 |
| 2005/0048010 | A1 * | 3/2005 | Kliss et al. ..................... 424/59 |
| 2008/0254295 | A1 | 10/2008 | Hibst et al. |
| 2010/0015188 | A1 | 1/2010 | Izu et al. |
| 2010/0056361 | A1 | 3/2010 | Izu et al. |
| 2010/0209710 | A1 | 8/2010 | Izu et al. |

FOREIGN PATENT DOCUMENTS

| JP | 02-092810 | 4/1990 |
| JP | 06-218276 | 8/1994 |
| JP | 2004-035632 | 2/2004 |
| JP | 2004-182483 | 7/2004 |
| JP | 2004-292282 | 10/2004 |
| JP | 2005-060145 | 3/2005 |
| JP | 2006-0008629 | 1/2006 |
| JP | 2007-197431 | 8/2007 |
| JP | 2007-217380 | 8/2007 |
| WO | 2007/036475 A1 | 4/2007 |
| WO | WO 2007139719 A1 * | 12/2007 |
| WO | 2008/041729 A1 | 4/2008 |

OTHER PUBLICATIONS

Ho et al., Chem. Mater., 2005, 17, 4514-4522.*
Anderson et al. Journal of Applied Polymer Science, 1979, 23, 2453-2462.*
Yoshida et al., Applied Optics, 1996, 35(9), 1500-1506.*
Yang et al., "Synthesis of homogeneous PVP-capped $SnS_2$ submicron particles via microwave irradiation", Materials Letters, 60, 2006, pp. 3714-3717.
Zhang et al., "PVP Protective Mechanism of Ultrafine Silver Powder Synthesized by Chemical Reduction Process", Journal of Solid State Chemistry, 121, 1996, pp. 105-110.
Tao et al., "New procedure towards size-homogeneous and well-dispersed nickel oxide nanoparticles of 30nm", Materials Letters, 58, 2004, pp. 3326-3228.
Xi et al., "Selected-control synthesis of $PbO_2$ submicrometer-sized hollow spheres and $Pb_3O_4$ microtubes", Inorganic Chemistry Communications, 7, 2004, pp. 607-610.
Guo et al., "Synthesis and Characterization of Poly(vinylpyrrolidone)-Modified Zinc Oxide Nanoparticles", Chemistry of Materials, 2000, vol. 12, No. 8, pp. 2268-2274.

(Continued)

*Primary Examiner* — Abigail Fisher
(74) *Attorney, Agent, or Firm* — Suzannah K. Sundby, Esq.; Smith, Gambrell & Russell, LLP (57) ABSTRACT

Disclosed herein are core-shell type zinc oxide microparticles, a dispersion containing such microparticles, and a production process and uses of the microparticles and the dispersion. As disclosed herein, the core-shell type zinc oxide microparticles have an average particle diameter of from 50 to 1,000 nm. The core is a secondary particle of spherical shape to the surface of which a polymer is attached as a shell. Methods for making the microparticles include the steps of: mixing together a zinc salt and a polymer in an organic solvent so as to obtain a mixture; and heating/refluxing the mixture at a predetermined temperature so as to cause core-shell type zinc oxide microparticles to precipitate, wherein the zinc salt is zinc acetate; and uses such as cosmetics, resins and fibers which contain the core-shell type zinc oxide microparticles and have an ultraviolet light blocking action.

15 Claims, 5 Drawing Sheets

(56) References Cited

OTHER PUBLICATIONS

Viswanatha et al., "Study of the Growth of Capped ZnO Nanocrystals: A Route to Rational Synthesis", Chemistry A European Journal, 2005, vol. 12, No. 1, pp. 180-186.
Jezequel et al., "Submicrometer zinc oxide particles: Elaboration in polyol medium and morphological characteristics", Journal of Materials Research, 1995, vol. 10, No. 1, pp. 77-83.
Yang et al., "Enhanced ultraviolet emission and optical properties in polyvinyl pyrrolidone surface modified ZnO quantum dots", Journal of Applied Physics, 2001, vol. 90, No. 9, pp. 4489-4493.
International Search report for PCT/JP2009/052087 mailed Apr. 21, 2009 w/ English language translation.

* cited by examiner

CORE-SHELL TYPE ZINC OXIDE MICROPARTICLE OR DISPERSION CONTAINING THE MICROPARTICLE, AND PRODUCTION PROCESS AND USE OF THE MICROPARTICLE OR THE DISPERSION

TECHNICAL FIELD

The present invention relates to core-shell type zinc oxide microparticles, a dispersion containing such microparticles, and a production process and uses of the microparticles or the dispersion. The invention relates more particularly to core-shell type zinc microparticles capable of being used in products such as catalysts, antireflection coatings and ultraviolet light-blocking agents, to a dispersion containing such microparticles, to a process for producing such zinc oxide microparticles or a dispersion containing such microparticles for the purpose of manufacturing such products, and to such products.

BACKGROUND ART

Zinc oxide is well-known as a material used in UV blockers. For example, the prior-art references disclose applications for UV blockers in which zinc oxide is used (see Patent Documents 1 and 2). UV blockers are employed in cosmetics, and come into contact with human skin. Accordingly, it is desirable that the ingredients be chemically inert.

Although several reports have hitherto appeared on the synthesis of zinc oxide nanoparticles (see Patent Documents 3 to 5), no reports have appeared to date on zinc oxide microparticles which are spherical and have a particle diameter of about 50 to 1,000 nm and a good dispersibility in any liquid, such as water or an organic solvent, or on zinc oxide microparticle dispersions.

When a dispersion of zinc oxide particles is produced for the above applications, a stable dispersion cannot be obtained by the conventional method of simply dispersing fine particles of dried zinc oxide in a dispersion medium. This is because the zinc oxide particles aggregate, and it is necessary to break up these aggregations in order to obtain a stable dispersion.

Whether nanoparticles are synthesized by a gas phase process or a liquid phase process, they generally aggregate strongly unless aggregation is controlled following formation of the nanoparticles. Once the nanoparticles have strongly aggregated, it is generally difficult to break up the aggregations even by suitable treatment of the particles.

The prior-art reference discloses a technique for mechanically breaking up aggregations using ceramic beads (see Patent Document 6), but the problem in this case is the possibility of contamination by impurities. Moreover, a dispersant must be added to the solvent. For these reasons, zinc oxide microparticles which easily disperse (are resistant to aggregation) must be synthesized in such a way that aggregations do not have to be broken up by mechanical means or by dispersant addition.

Because nanoparticles are difficult to separate once they have aggregated, it should be possible to obtain easily dispersible zinc oxide particles by treating them to control aggregation before the nanoparticles aggregate; that is, as they are being produced.

If a dispersion medium in which a polymer has been dissolved is used as the locus of the reaction in this case, aggregation can be controlled as the zinc oxide microparticles are being produced, thereby presumably enabling a stable dispersion of zinc oxide microparticles to be obtained. Moreover, even if the zinc oxide microparticle dispersion is dried, it will probably be easy to re-disperse in a dispersion medium because it has been subjected to aggregation control treatment.

Instances where such a concept is used in a sol-gel process or a hydrolysis process have been reported (see Non-Patent Documents 1 to 4, Patent Document 7), although these reports do not relate to zinc oxide. No cases have been found in which such a concept has been applied to a refluxing process for precipitating zinc oxide microparticles.

Also, ultrafine particles of metal oxide and a production process for the same, and fine particles of metal oxide have been disclosed in respective prior-art documents (see Patent Documents 8 and 9). In these prior-art documents, the particles are spherical secondary particles having a particle diameter of about 50 to 1,000 nm and a small particle diameter distribution (standard deviation of particle diameter) which are formed by the aggregation of metal oxide primary particles having a particle diameter of about 10 to 20 nm. No mention whatsoever has been made of core-shell type zinc oxide microparticles having a good dispersibility in liquid or of core-shell type zinc oxide microparticle dispersions.

Patent Document 1: Japanese Patent Application Laid-open No. 2007-217380
Patent Document 2: Japanese Patent Application Laid-open No. 2007-197431
Patent Document 3: Japanese Patent Application Laid-open No. 2004-292282
Patent Document 4: Japanese Patent Application Laid-open No. 2004-182483
Patent Document 5: Japanese Patent Application Laid-open No. 2005-060145
Patent Document 6: Japanese Patent Application Laid-open No. 2004-35632
Patent Document 7: Japanese Patent Application Laid-open No. H2-92810
Patent Document 8: Japanese Patent Application Laid-open No. H6-218276
Patent Document 9: Japanese Patent Application Laid-open No. 2006-8629
Non-Patent Document 1: H. Yang, C. Huang, X. Su, *Materials Letters*, 60 (2006) 3714
Non-Patent Document 2: Z. T. Zhang, B. Zhao, L. M. Hu, J. *Solid State Chem.*, 121 (1996) 105
Non-Patent Document 3: D. L. Tao, F. Wei, *Mater. Lett.*, 58 (2004) 3226
Non-Patent Document 4: G. C. Xi, Y. Y. Peng, L. Q. Xu, M. Zhang, W. C. Yu, Y. T. Qian, *Inorg. Chem. Commun.*, 7 (2004) 607

In light of these circumstances, the inventors conducted extensive research aimed at developing a process for producing nanosize zinc oxide particles which control nanoparticle aggregation and have long-term stability, and for producing dispersions of such particles. As a result, they have discovered that the use of a refluxing technique provides numerous advantages, including the ability to use an organic solvent and the absence of a need for a reaction initiator. They have also found that an inexpensive acetate may be suitably used as the starting material instead of an expensive alkoxide, thereby enabling the production of core-shell type zinc oxide microparticles which control nanoparticle aggregation, and of a dispersion of such microparticles. Further research by the inventors ultimately led to the present invention.

DISCLOSURE OF THE INVENTION

It is therefore an object of the present invention to provide core-shell type zinc oxide microparticles which have a spherical shape, a particle diameter of about 50 to 1,000 nm and a small particle size distribution (standard deviation of particle diameter), wherein the core is a secondary particle that is spherical and of uniform size, and which has a good dispersibility in a liquid. A further object of the invention is to provide a dispersion of such zinc oxide microparticles. Still further objects are to provide a process for producing the core-shell zinc oxide microparticles and a dispersion of the zinc oxide microparticles, which process applies a refluxing technique to the concept described above, and to provide uses of the microparticles and the dispersion.

To resolve the problems mentioned above, the present invention comprises the following technical means.

(1) Core-shell type zinc oxide microparticles, characterized in that 1) a core portion thereof is a secondary particle formed by a spherical aggregation of primary particles of zinc oxide, 2) the secondary particle is of uniform shape, 3) a polymer layer that forms a shell portion exists on a surface of the secondary particle, and 4) the microparticles have an average particle diameter of from 50 nm to 1,000 nm.

(2) The core-shell type zinc oxide microparticles according to (1) above, wherein the polymer layer is composed of a polymer which is polyvinylpyrrolidone (PVP), hydroxypropyl cellulose (HPC) or polyethylene glycol (PEG), or of a polymer crosslinked with the polymer or with diethylene glycol (DEG), does not separate from the secondary particle of the core portion even when the microparticles are subjected to rinsing, and is present in a proportion of from 5 wt % to 10 wt %.

(3) The core-shell type zinc oxide microparticles according to (1) above, wherein the primary particles have a diameter of from 10 to 20 nm and the secondary particle has a diameter coefficient of variation of 0.1 or less.

(4) A core-shell type zinc oxide microparticle powder as a dry powder containing the core-shell type zinc oxide microparticles defined in any one of (1) to (3) above, which has the quality of dispersing well in a dispersion medium to which dispersant is not added.

(5) A core-shell type zinc oxide microparticle dispersion comprising the core-shell type zinc oxide microparticles or the core-shell type zinc oxide microparticle powder defined in any one of (1) to (4) above, which is dispersed in a dispersion medium.

(6) The core-shell type zinc oxide microparticle dispersion according to (5) above, wherein the dispersion medium is any one of water, ethanol, terpineol and ethylene glycol, or a mixed solution of a plurality thereof.

(7) A cosmetic having an ultraviolet light blocking action, comprising the microparticles, microparticle powder or microparticle dispersion defined in any one of (1) to (6) above.

(8) A resin or fiber having an ultraviolet light blocking action, comprising the microparticles, microparticle powder or microparticle dispersion defined in any one of (1) to (6) above.

(9) A process for producing core-shell type zinc oxide microparticles, a zinc oxide microparticle powder or a zinc oxide microparticle dispersion, which is a process for producing the core-shell type zinc oxide microparticles, zinc oxide microparticle powder or zinc oxide microparticle dispersion defined in any one of (1) to (8) above, comprising the steps of:

mixing together a zinc salt and a polymer in a high-boiling-point organic solvent so as to obtain a mixture;

and heating/refluxing the mixture at a temperature of at least 160° C. so as to cause the zinc oxide microparticles to precipitate and form a core-shell structure.

(10) The process for producing zinc oxide microparticles according to (9) above, wherein the zinc salt is zinc acetate, the polymer is polyvinylpyrrolidone (PVP), hydroxypropyl cellulose (HPC) or polyethylene glycol (PEG), and the high-boiling-point organic solvent is diethylene glycol (DEG).

(11) The process for producing zinc oxide microparticles according to (9) or (10) above, wherein the polymer has a concentration (weight of polymer added per unit volume of organic solvent) of from 100 kg/m$^3$ to 140 kg/m$^3$.

(12) The process for producing zinc oxide microparticles according to (9) or (10) above, wherein the polymer has a polyethylene glycol-equivalent average molecular weight of from 4,000 to 5,000.

The invention is described below in greater detail.

Figure 1:
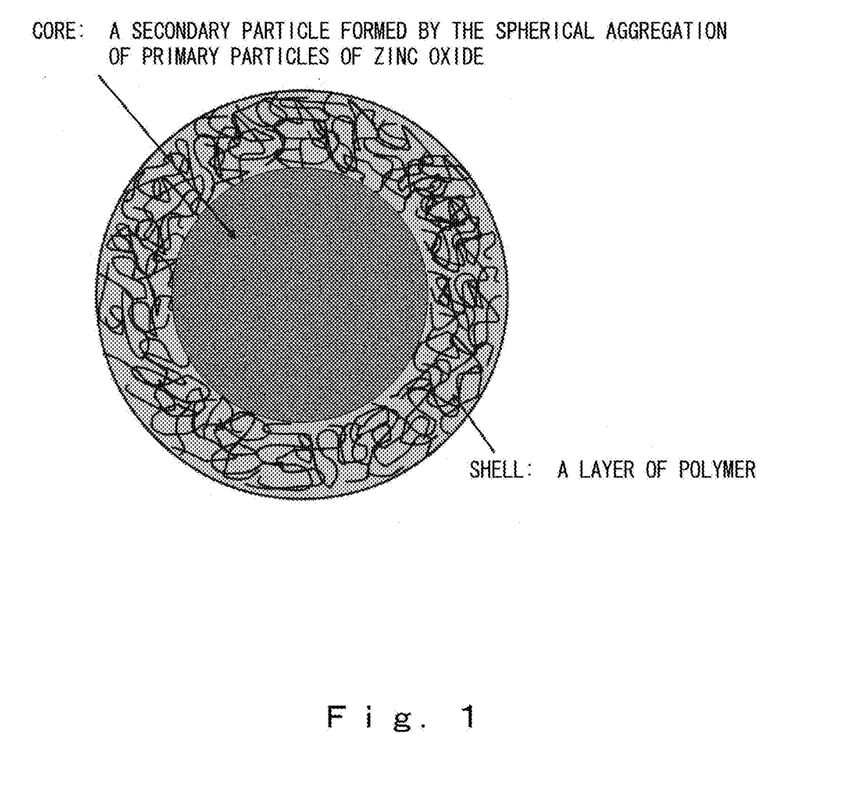
FIG. 1 shows a schematic diagram of a core-shell structure.

As used herein, "core-shell type zinc oxide microparticle" is defined as referring to a microparticle in which a secondary particle formed by the spherical aggregation of primary particles of zinc oxide has on the surface thereof a layer of polymer (see FIG. 1). This core-shell type zinc oxide microparticle differs from a particle composed of a polymer present on the surface of a primary particle or a secondary particle of irregularly aggregated primary particles.

A prior-art reference discloses a composite particle composed of a polymeric compound coated on the surface of a primary particle or an agglomerate. However, this primary particle or agglomerate is not spherical, having an irregular shape. The reason is that, in the production method disclosed in the aforementioned reference, the metal oxide microparticles which have been synthesized beforehand are dispersed or disintegrated using a dispersing apparatus such as a bead mill.

In this dispersion step, the primary particles or primary particle agglomerates are disintegrated, but the primary particle agglomerates following disintegration cannot be made spherical and given a uniform size as in the case of the core-shell type zinc oxide microparticles of the present invention. Moreover, the content of the coated polymer is indicated in the above reference as being at least 25 wt %. By contrast, in the present invention, as subsequently mentioned, the polymer content is from 5 to 10 wt %; hence, the layer of polymer accounts for less than 25 wt %. This is because the polymer which readily detaches has been removed by rinsing. This too is a major difference with the composite particles of the above document.

The inventive core-shell type zinc oxide microparticles having an average particle diameter of from 50 nm to 1,000 nm are characterized in that a secondary particle of the core portion has a spherical shape and is uniform in size, and the polymer serving as the shell portion is attached to the surface of the zinc oxide secondary particle. The core-shell type zinc oxide microparticle dispersion of the invention is characterized by being composed of the above-described core-shell type zinc oxide microparticles dispersed in a dispersion medium.

The core-shell type zinc oxide microparticle powder of the invention is characterized by having the quality of dispersing well in a dispersion medium to which dispersant is not added. Furthermore, the core-shell type zinc oxide microparticle production process of the invention is characterized by including the steps of mixing together a zinc salt and a polymer in a high-boiling-point organic solvent so as to obtain a mixture, and heating/refluxing the mixture at a temperature of at least 160° C. so as to cause the zinc oxide microparticles to precipitate. In a preferred embodiment of this invention, the zinc salt is zinc acetate.

As used herein, "core-shell type zinc oxide microparticle dispersion" refers to a dispersion obtained by dispersing the core-shell type zinc oxide microparticles as the dispersoid in a dispersion medium. This dispersion may alternatively be referred to as a suspension or a sol. In cases where the concentration of microparticles is high, the dispersion may be called as a paste.

First, the process for producing the core-shell type zinc oxide microparticles of the invention is described. The starting materials are zinc acetate, a high-boiling-point organic solvent, and a polymer. Of these, the zinc acetate may be a commercially available substance, and is generally a hydrate.

To obtain metal ion-doped zinc oxide microparticles, a metal salt is added in addition to the zinc acetate. High-boiling-point organic solvents include diethylene glycol (DEG) and glycerol. DEG is more preferred. Also, the polymer is preferably one that dissolves in the organic solvent. Examples include polyvinylpyrrolidone (PVP), hydroxypropyl cellulose (HPC) and polyethylene glycol (PEG). PVP and HPC are more preferred.

These starting materials are mixed and dissolved. In this step, a zinc salt and a polymer are mixed in a high-boiling-point organic solvent so as to obtain a mixture. The concentration of zinc acetate at this time is preferably from 0.04 to 0.2 kmol/m$^3$. The polymer concentration is preferably from 100 kg/m$^3$ to 140 kg/m$^3$.

As used herein, "polymer concentration" is defined as the weight of polymer added per unit volume of solvent. The reason for setting the polymer concentration in a range of from 100 kg/m$^3$ to 140 kg/m$^3$ is that below this range, the dispersibility of the microparticles may worsen. On the other hand, if the polymer concentration is higher than this range, spherical zinc oxide microparticles cannot be obtained.

Next, the above mixture is heated/refluxed at a temperature of from 160 to 200° C. This is a step in which the zinc oxide is precipitated by heating and refluxing at a predetermined temperature. Generally, an alkali such as sodium hydroxide or ammonia is added when inducing an oxide to precipitate. However, this invention is characterized in that such addition is not necessary. By adding sodium hydroxide or the like, the nanoparticles ultimately obtained may be contaminated with sodium. In this invention, because there is no need for alkalis and the like, contamination by such impurities is unlikely to occur.

The heating/refluxing time is from about 10 to 120 minutes. At a short heating/refluxing time, there is a possibility that a large amount of unreacted zinc ions will remain. Conversely, if the heating/refluxing time is too long, there is a possibility that organic compounds of zinc will form. For this reason, the heating/refluxing time is preferably from about 10 to 120 minutes, and more preferably from 30 to 120 minutes.

During heating and refluxing, the liquid mixture becomes cloudier. Heating/refluxing is carried out for a predetermined time and is followed by cooling. In this way, there can be obtained a core-shell type zinc oxide microparticle dispersion of core-shell type zinc oxide microparticles dispersed in an organic solvent within which a polymer has been dissolved. The mechanism by which the core-shell type zinc oxide microparticles form is thought to be as follows.

1. Primary particles of zinc oxide nucleate in the high-boiling-point organic solvent (polyol) containing a uniformly dissolved polymer.
2. The primary particles spherically aggregate. The primary particles continually nucleate at this time as well.
3. The nucleated primary particles gather spherically at the surface of an agglomerate (secondary particle).
4. At this time, with the zinc oxide acting as a catalyst at the surface of the secondary particle, the polymer and/or organic solvent gives rise to crosslinking reactions, resulting in the formation of a strong polymer layer.
5. When the strong polymer layer has fully developed, aggregation ceases to occur, giving a core-shell type zinc oxide microparticle.

In the present invention, the core-shell type zinc oxide microparticles are defined as particles characterized by having a core portion that is a secondary particle formed by the spherical aggregation of primary particles of zinc oxide, which secondary particle is of a uniform shape, and a shell portion composed of a layer of polymer on the surface of the secondary particle, and by having an average particle diameter of from 50 nm to 1,000 nm.

The polymer layer serving as the shell portion is composed of polyvinylpyrrolidone (PVP), hydroxypropyl cellulose (HPC), or a related polymer. Here, "related polymer" is exemplified by polymers formed by the mutual crosslinking of PVP, polymers formed by the mutual crosslinking of HPC, polymers formed by crosslinking PVP or HPC with a polyol and polymers formed by the mutual crosslinking of polyols, and encompasses various types of such polymers.

Heat is thought to be required for zinc oxide to trigger catalytic activity. This is why heating/refluxing at a temperature of at least 160° C. is necessary. In cases where the heating/refluxing temperature is low, even if primary particles have formed, they will not become core-shell type particles. If the primary particles do not aggregate, formation of the inventive core-shell type zinc oxide microparticles will not occur.

In such a case, because a large amount of unreacted polymer is present, vaporizing the solvent will result in the formation of a zinc oxide-polymer composite composition made up of primary particles which remain within a polymer matrix. This clearly differs from core-shell type zinc oxide microparticles.

Even if aggregation should arise in this case, because there are no catalyst reactions at the zinc oxide surface, a polymer layer is unable to form, resulting in aggregated particles of irregular shape. This type of metal oxide-polymer composite composition is disclosed in prior-art documents, but differs fundamentally from the present invention.

As shown in the subsequently described working examples of the invention, because core-shell type zinc oxide microparticles do not form below some critical temperature, heating/refluxing at an elevated temperature is essential. In the core-shell type zinc oxide microparticle dispersion obtained right after such heating and refluxing, the dispersion medium is the organic solvent used in heating and refluxing. For example, if heating and refluxing is carried out with diethylene glycol (DEG), the dispersion medium is DEG.

If there is a desire to change the dispersion medium to some other dispersion medium, this may be done by replacing the dispersion medium with another dispersion medium. Such dispersion medium substitution may be carried out by, for example, using a technique such as centrifugal separation to separate the dispersion medium and the dispersoid, removing the dispersion medium, and adding the desired dispersion medium. At this time, the polymer forming the shell portion can not be separated off with rinsing, and is inseparable from the core.

Some of the polymer used in the heating/refluxing is thought to remains in the dispersion medium, in addition to which unreacted zinc ions are also thought to remain. The excess polymer may be removed by repeatedly carrying out centrifugal separation and solvent substitution. The core-shell type zinc microparticles acting as the dispersoid in the dispersion obtained by the above-described method are spherical. "Particle diameter" refers herein to the diameter of the core-shell type zinc oxide microparticles, as determined by scanning electron microscopic (SEM) observation.

The secondary particle that forms the core portion is an aggregation of primary particles, and is also sometimes called as a primary agglomerate. The primary particle diameter is from 10 to 20 nm. Each individual spherical zinc oxide microparticle serving as a core portion is a secondary particle, not a primary particle. The zinc oxide microparticles may be doped with metallic ions having a valence of from 1 to 5. Metallic ions such as sodium, calcium, yttrium, gadolinium, zirconium, hafnium and niobium may be used for such doping.

The shape, particle diameter and other properties of the zinc oxide microparticles can be ascertained by the following method. The particle diameter for the dispersion immediately after heating/refluxing may be determined by a dynamic light scattering (DLS) method. This particle diameter is the diameter of particles individually present within the dispersion medium. This particle diameter generally differs from the particle diameter of microparticles observed with a SEM or the like. The reason is that microparticles often additionally aggregate within the dispersion medium; in such cases, the size of the particles resulting from aggregation of the microparticles emerges as a result.

A collection of secondary particles (microparticles) aggregated is sometimes called as a "secondary agglomerate." The refractive index and viscosity of the dispersion medium are necessary in the dynamic light scattering (DLS) method. A value described in a document may be used as the refractive index of the dispersion medium. On the other hand that the viscosity of the dispersion medium is identical with the viscosity of the dispersion, the value obtained by measuring the viscosity of the dispersion is employed.

In this way, the average particle diameter ($d_{average}$) and the standard deviation (s) are determined, from which the coefficient of variation c ($=s/d_{average}$) is calculated. A dry powder can be obtained by subjecting the dispersion prepared as described above about three times to centrifugal separation and re-dispersion in water or ethanol, followed by drying at, e.g., 80° C. The dry powder is examined with a SEM, and the shape of the particles as well as the average particle diameter and standard deviation are determined.

The core-shell type zinc oxide microparticles have an average particle diameter of from 50 nm to 1,000 nm. Moreover, core-shell type zinc oxide microparticles of uniform particle diameter, i.e., having a small particle diameter coefficient of variation, can be obtained in a frequency of one out of several synthetic experiments. The coefficient of variation in this case is 0.25 or less, and sometimes 0.10 or less. This can be confirmed by SEM observation of the dry powder. Also, the particle diameter in the dispersion medium is not more than twice that of the core-shell type zinc oxide microparticles. This indicates that the core-shell type zinc oxide microparticles are present within the dispersion medium in a substantially unaggregated state.

A polymer layer is, of course, present as the shell portion on the surface of the core-shell type zinc oxide microparticles. This can be investigated and confirmed for the dry powder by Fourier transform infrared spectrophotometric (FTIR) analysis and thermogravimetric (TG) analysis. The above-described dry powder is subjected about three times to centrifugal separation and re-dispersion in water or ethanol, following which excessive polymer not associated with the core-shell type zinc oxide microparticles is removed. Because of the drying carried out, the dispersion medium is also fully removed. The polymer layer is present in a content of preferably from 5 to 10 wt %.

The absorption peaks other than for zinc oxide which are observable in Fourier transform infrared spectrophotometry (FTIR) arise from what is present at the surface of the zinc oxide microparticles. The fact that such absorption peaks resemble absorption by the polymer, together with the existence of a weight change at temperatures above the boiling point of the dispersion medium, leads to the conclusion that polymer is attached to the surface of the zinc oxide microparticles.

Here, the polymer is preferably PVP, HPC, a polymer formed by the mutual crosslinking of PVP, a polymer formed by the mutual crosslinking of HPC, a polymer obtained by the crosslinking of PVP or HPC with a polyol, a polymer obtained by the mutual crosslinking of polyols, or a product obtained by the reaction of any of the above with zinc oxide.

The zinc oxide microparticles obtained by the invention are thought to be chemically inert on account of the fact that polymer is attached to the surface of the zinc oxide. Because UV blockers used in cosmetics come into direct contact with human skin, etc., it is desirable for the microparticles to be chemically inert. The zinc oxide microparticles obtained in the present invention appear to be highly suitable as a UV blocker.

In particular, PVP is known to be safe and harmless in humans. A zinc oxide microparticle dispersion in which PVP is coated on the surface of the microparticles is promising as a UV blocker. It is anticipated that products obtained by dispersing zinc oxide microparticles having a UV blocking effect in a resin or the like, and rendering the dispersion into a fibrous, bulk or other desired form will also have UV blocking effects.

The dry powder easily disperses even when re-dispersed in a dispersion medium. This is a property that differs from ordinary powders. In general, once a powder is dried, it strongly aggregates; as a result, even when an attempt is made to re-disperse the powder, it does not easily disperse. However, the dry powder of the invention can be easily dispersed using only an ultrasonic homogenizer; that is, a dispersant is not required.

The dispersion medium in this case may be any suitable dispersion medium. Preferred example is any one of water, ethanol, terpineol and ethylene glycol, and mixed solutions obtained by mixing a plurality thereof. Even when the above core-shell type zinc oxide microparticles are re-dispersed in these dispersion media, the particle diameter within the dispersion medium is not more than twice the particle diameter determined by SEM observation, indicating that the core-shell type zinc oxide microparticles are present in an unaggregated state.

In this way, the re-dispersibility of the dry powder appears to be attributable to the presence of polymer in the shell portion of the core-shell type zinc oxide microparticles. Moreover, firing at a temperature higher than 500° C. completely removes the polymer corresponding to the shell portion. This results in the formation of spherical zinc oxide microparticles. These zinc oxide microparticles are secondary particles formed by the spherical aggregation of primary particles.

In the case of microparticles composed of primary particles of zinc oxide which are simply present within a polymer matrix, after firing, only the zinc oxide primary particles remain; even if these do aggregate, they cannot become spherical. Therefore, core-shell type zinc oxide microparticles and zinc oxide-polymer composite compositions have fundamentally different structures.

When oxide microparticles are employed in various products, they are almost never handled as a powder; rather, they are generally dispersed in a liquid and handled as a dispersion. However, a problem with oxide microparticles is that they have an increasing tendency to aggregate the smaller the particle diameter. There are no examples in the prior art of the development of zinc oxide microparticles which are spherical, have a particle diameter of about 50 to 1,000 nm and have a good dispersibility in a liquid such as water or an organic solvent, or of dispersions of such zinc oxide microparticles. Moreover, in prior-art processes, microparticles are formed by adding a basic substance such as sodium hydroxide or potassium hydroxide at the time of production, which is thought to result in contamination of the oxide by impurities such as sodium and potassium.

By contrast, the present invention provides core-shell type zinc oxide microparticles wherein the core portion is a secondary particle formed by the spherical aggregation of zinc oxide primary particles, the secondary particles being of uniform shape and having on a surface thereof a layer of polymer as the shell portion, which microparticles have an average particle diameter of from 50 nm to 1,000 nm. The invention also provides a dispersion containing such microparticles, and a process for producing the microparticles and the dispersion. The core-shell type zinc oxide microparticles of the invention may be suitable employed in, for example, catalysts, antireflection coatings and UV blockers.

The invention achieves the following effects.
(1) It can provide core-shell type zinc oxide microparticles having a particle diameter of about 50 nm to 1,000 nm, a spherical shape and a good dispersibility in liquids, and a dispersion of such microparticles.
(2) It can provide a dry powder of core-shell type zinc oxide microparticles that readily re-disperse.
(3) It can provide a dispersion of core-shell type zinc oxide microparticles dispersed in any dispersion medium.
(4) It can provide high-viscosity core-shell type zinc oxide microparticle dispersions, i.e., core-shell type zinc oxide microparticle pastes.
(5) It can provide a simple process for producing core-shell type zinc oxide microparticles and for producing a dispersion of such zinc oxide microparticles.
(6) It can obtain a high-concentration zinc oxide microparticle dispersion.
(7) By firing and oxidative removal of the polymer, it can provide spherical zinc oxide microparticles.
(8) The present invention is able to provide a production process for zinc oxide microparticles and dispersions containing such microparticles which can be employed in, for example, catalysts, antireflection coatings and UV blockers, and is also able to provide such products.

BEST MODE FOR CARRYING OUT THE INVENTION

Working examples of the invention are given below by way of illustration, although the invention is in no way limited by these examples.

Polyvinylpyrrolidone (PVP; Sigma-Aldrich) and $Zn(CH_3COO)_2 \cdot 2H_2O$ (zinc acetate dihydrate; Wako Pure Chemical Industries) were added to 30 $cm^3$ of diethylene glycol (DEG; Wako Pure Chemical Industries) and stirred. The concentration of polymer added was 120 $kg/m^3$. The PVP had an average molecular weight (catalog value) of 10,000. The concentration of $Zn(CH_3COO)_2 \cdot 2H_2O$ was 0.10 $kmol/m^3$ (1 $kmol/m^3$=1 mol/L).

The above mixture was heated and refluxed at 180° C. for 20 minutes. The mixture was then cooled, giving a core-shell type zinc oxide microparticle dispersion. To remove unreacted material and excess PVP, the dispersion was subjected to centrifugal separation at 18,000 rpm, then rinsed with water and ethanol. After rinsing, drying was carried out at 80° C., giving a powder. The particle size distribution of dispersed particles within the dispersion immediately after refluxing was examined by the dynamic light scattering (DLS) method. In addition, the dry powder was examined with a SEM, and the particle size distribution was determined from the resulting images.

Figure 2:
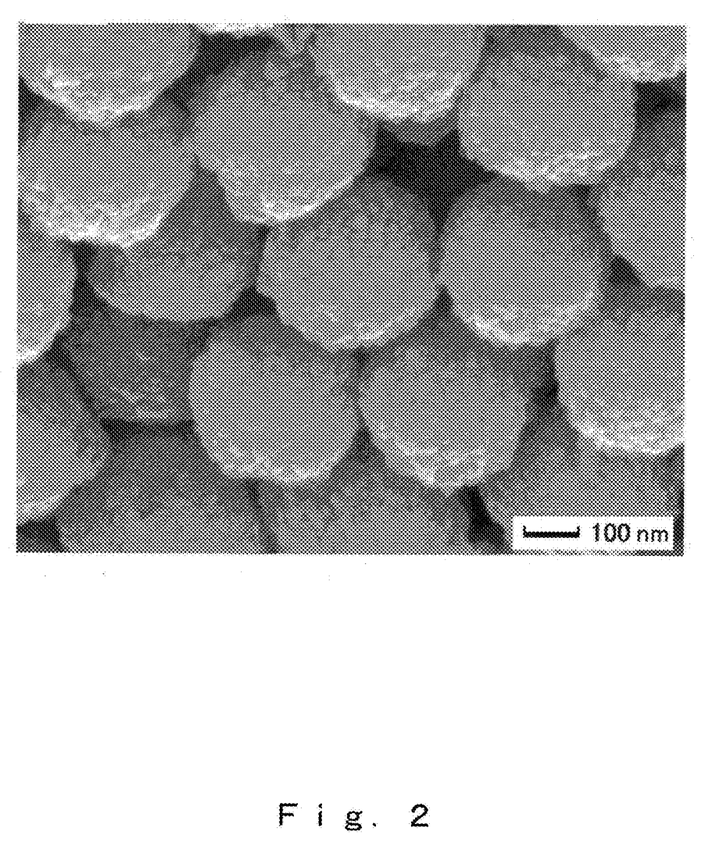
FIG. 2 shows a SEM of the dry powder of Example 1.

The dispersion immediately after refluxing had an average particle size, as determined by the DLS method, of 282 nm. FIG. 2 shows an SEM image of the dry powder. Spherical microparticles were observed. The particle diameter determined from the SEM image was 336 nm, which was substantially the same as the average particle diameter of microparticles within the dispersion immediately after refluxing. This indicates that the spherical microparticles observed by SEM had dispersed within the dispersion without aggregating. The experiment was carried out six times under the experimental conditions in Example 1. In one of these six runs, the coefficient of fluctuation in the particle diameter of the cry powder was less than 0.1. That is, the microparticles were confirmed to be of uniform diameter and monodispersed.

Figure 3:
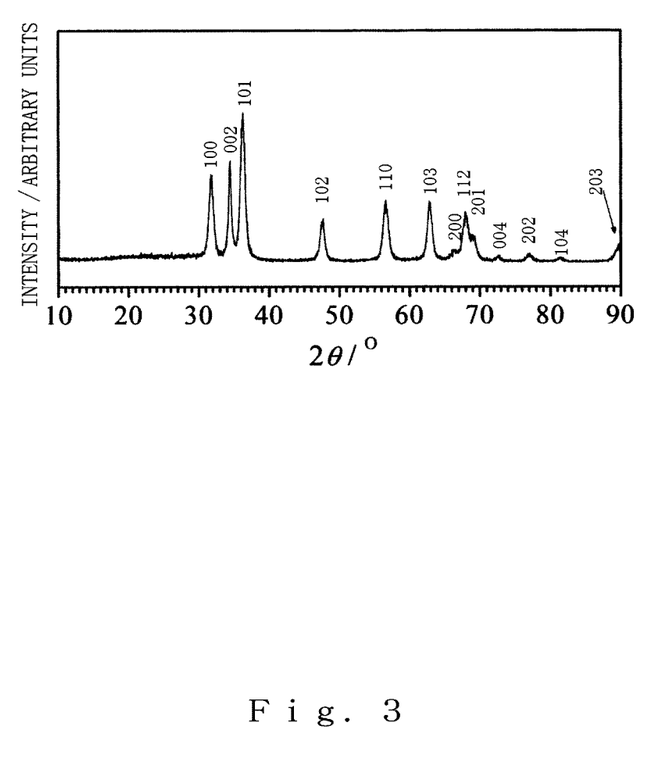
FIG. 3 shows an XRD pattern for the dry powder of Example 1.

FIG. 3 shows the XRD pattern for the dry powder. This is the diffraction pattern of a wurtzite structure, confirming that the powder was zinc oxide. Zinc oxide was confirmed to be present in the microparticles within the dispersion immediately after refluxing, and in the dry powder. The crystallite diameter was calculated from the diffraction peak widths, and confirmed to be 14 nm.

Figure 4:
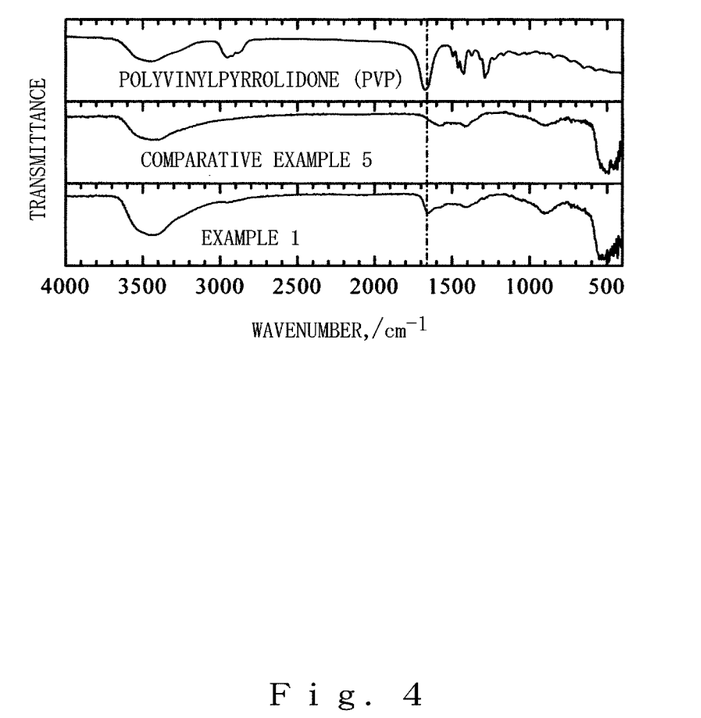
FIG. 4 shows an IR spectrum of the dry powder in Example 1.

FIG. 4 shows the IR spectrum of the dry powder obtained in this example. Also shown here is the IR spectrum for the dry powder obtained in Comparative Example 5, which is subsequently described. In Comparative Example 5, synthesis was carried out under basically the same synthesis conditions as in Example 1, but without the addition of PVP. FIG. 4 additionally shows the IR spectrum for PVP. An absorption peak was observed at 1600 $cm^{-1}$ in the IR spectrum for the dry powder of Example 1.

On the other hand, an absorption peak was not observed in the IR spectrum for the dry powder in Comparative Example 5. Because an absorption peak is observable at 1600 $cm^{-1}$ in the IR spectrum for PVP as well, the peak at 1600 $cm^{-1}$ observed in Example 1 but not observed in Comparative Example 5 was confirmed to be an absorption peak associated with PVP.

Figure 5:
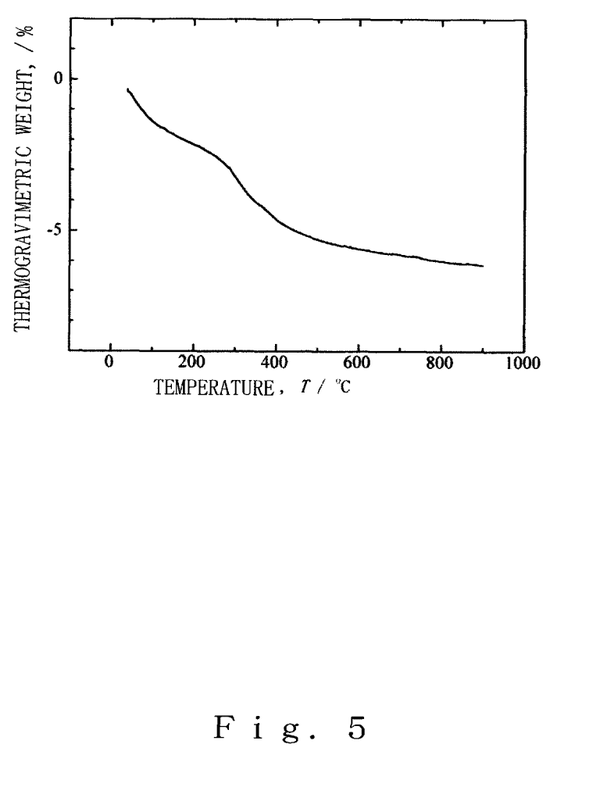
FIG. 5 shows a TG curve for the dry powder in Example 1.

The results of TG analysis are shown in FIG. 5. When the temperature was raised to 900° C., the weight decreased by about 6%. In addition, the SEM image of the powder after firing at 500° C. showed spherical particles. Judging overall from this and the FTIR and TG results, either PVP or a polymer related to PVP is present in the microparticles of Example 1. As a result, the microparticles obtained in Example 1 were confirmed to be core-shell type zinc oxide microparticles having a zinc oxide core and a polymer shell.

The dispersion stabilities in water were investigated for a dispersion of the dry powder of Example 1 re-dispersed in water and for a dispersion of the dry powder of Comparative Example 5 re-dispersed in water. Here, 0.02 g of the dry powder of Example 1 or Comparative Example 5 was dispersed in 2 mL of water, and the manner in which precipitation occurred in the dispersion was observed.

Because precipitate remained in both samples even after 3 minutes of treatment in an ultrasonic homogenizer (output, 9.5), the samples were subjected to an additional 3 minutes of treatment (output, 9.5), causing full dispersion to occur in both samples. The samples were subsequently left at rest. When 150 minutes had elapsed, only a slightly transparent layer was present in Example 1. By contrast, in Comparative Example 5, the sample had separated into a slightly transparent layer, a faint cloudy layer, and a dense cloudy layer.

This confirmed that the sample in Comparative Example 5 precipitated more rapidly. When the samples were held in this state for two days, both samples completely precipitated. However, in Example 1, the precipitate was soft and easily re-dispersed. In Comparative Example 5, the precipitate was hard and most of it remained at the bottom even when the container was shaken. This demonstrated that the re-dispersibility was good in Example 1.

This difference in re-dispersibility is presumably due to the presence of polymer from PVP at the surface of the zinc oxide. The particle size distribution of a dispersion obtained by re-dispersion in water was examined by the DLS method, whereupon the particle diameter was 393 nm, demonstrating that the particles were substantially unaggregated.

Examples 2 to 8

In Examples 2 to 8, experiments were carried out in which the concentration of the zinc acetate dihydrate, refluxing time and refluxing temperature were varied based on the experimental conditions in Example 1. The experimental conditions are shown in Table 1. In each of these examples, the core of the microparticles obtained was zinc oxide, and the shape of the microparticles was spherical.

The particle diameters ranged from 300 to 700 nm. Table 2 shows the experimental results in detail. The experiment s were carried out six times under the experimental conditions in Example 2. In two of these experimental runs, the coefficient of fluctuation in the particle diameter determined from SEM images of the microparticles obtained was less than 0.3. Moreover, in one of the experimental runs, the coefficient of fluctuation was less than 0.15, indicating that uniform particle diameters were obtained.

TABLE 1

| Example | Dispersion medium | Polymer | Average molecular weight of polymer | Polymer Concentration (kg/m$^3$) | Concentration of zinc acetate hydrate (kmol/m$^3$) | Other added substances | Refluxing time | Refluxing Temperature (° C.) |
| --- | --- | --- | --- | --- | --- | --- | --- | --- |
| Example 1 | DEG | PVP | 10,000 | 120.5833 | 0.100284 | | 20 min | 180 |
| Example 2 | DEG | PVP | 10,000 | 120.5633 | 0.050157 | | 20 min | 180 |
| Example 3 | DEG | PVP | 10,000 | 120.6567 | 0.100679 | | 2 h | 180 |
| Example 4 | DEG | PVP | 10,000 | 120.5633 | 0.101317 | | 10 min | 180 |
| Example 5 | DEG | PVP | 10,000 | 121.37 | 0.050552 | | 2 h | 180 |
| Example 6 | DEG | PVP | 10,000 | 121.4767 | 0.051463 | | 1 h | 160 |
| Example 7 | DEG | PVP | 10,000 | 120.3833 | 0.100466 | | 24 min | 160 |
| Example 8 | DEG | PVP | 10,000 | 120.29 | 0.100815 | | 15 min | 199 |
| Example 9 | DEG | PVP | 55,000 | 120.04 | 0.100223 | | 2 h | 180 |
| Example 10 | DEG | PVP | 360,000 | 120.0367 | 0.100907 | | 2 h | 180 |
| Example 11 | DEG | HPC | 15,000-30,000 | 120.04 | 0.101165 | | 2 h | 180 |
| Comp. Ex. 1 | DEG | PVP | 10,000 | 120.57 | 0.100724 | 1 mL water | 15 min | 180 |
| Comp. Ex. 2 | DEG | PVP | 10,000 | 120.4833 | 0.1008 | 1 mL water | 15 min | 180 |
| Comp. Ex. 3 | EG | PVP | 10,000 | 120.5833 | 0.59976 | | 15 min | 180 |
| Comp. Ex. 4 | EG | PVP | 10,000 | 120.4133 | 0.100603 | | 2 h | 150 |
| Comp. Ex. 5 | DEG | none | | | 0.100572 | | 20 min | 180 |
| Comp. Ex. 6 | DEG | PVP | 10,000 | 120.1667 | 0.050856 | | 6.4 h | 140 |
| Comp. Ex. 7 | DEG | none | | | 0.050598 | | 20 min | 180 |
| Comp. Ex. 8 | DEG | PVP | 55,000 | 120.15 | 0.60055 | | 30 min | 180 |
| Comp. Ex. 9 | DEG | PVP | 55,000 | 600.15 | 0.10036 | | 2 h | 180 |
| Comp. Ex. 10 | DEG | PVP | 55,000 | 120.59 | 0.101225 | | 20 min | 180 |

TABLE 2

| Example | Product | Shape of oxide | Particle diameter determined from SEM image (nm) | CV of particle diameter determined from SEM image | Particle diameter determined by DLS method |
| --- | --- | --- | --- | --- | --- |
| Example 1 | zinc oxide | spherical | 336 | 0.078 | 282 |
| Example 2 | zinc oxide | spherical | 660 | 0.147 | 559 |
| Example 3 | zinc oxide | spherical | 384 | 0.362 | 335 |
| Example 4 | zinc oxide | spherical | 467 | 0.378 | 356 |
| Example 5 | zinc oxide | spherical | 625 | 0.421 | 457 |
| Example 6 | zinc oxide | spherical | 440 | 0.322 | |

TABLE 2-continued

| Example | Product | Shape of oxide | Particle diameter determined from SEM image (nm) | CV of particle diameter determined from SEM image | Particle diameter determined by DLS method |
|---|---|---|---|---|---|
| Example 7 | zinc oxide | spherical | 550 | 0.517 | 374 |
| Example 8 | zinc oxide | spherical | 600 | 0.41 | 434 |
| Example 9 | zinc oxide | spherical | 503 | 0.409 | 255 |
| Example 10 | zinc oxide | spherical | 752 | 0.549 | |
| Example 11 | zinc oxide | spherical | 405 | 0.405 | 235 |
| Comp. Ex. 1 | zinc oxide | partially non-spherical | 570 | 0.219 | 506 |
| Comp. Ex. 2 | zinc oxide | partially non-spherical | 1,050 | 0.093 | 607 |
| Comp. Ex. 3 | zinc oxide | non-spherical | | | |
| Comp. Ex. 4 | zinc oxide + unknown phase | non-spherical | | | |
| Comp. Ex. 5 | zinc oxide | spherical | 436 | 0.48 | 610 |
| Comp. Ex. 6 | unknown | non-spherical | | | |
| Comp. Ex. 7 | unknown | partially non-spherical | | | |
| Comp. Ex. 8 | zinc oxide | football-shapd | | | 991 |
| Comp. Ex. 9 | zinc oxide | partially non-spherical | 830 | 0.224 | |
| Comp. Ex. 10 | zinc oxide | partially non-spherical | | | |

Examples 9 and 10

As Examples 9 and 10, experiments based on Example 3 were carried out in which the average molecular weight of PVP was varied. The experimental conditions are shown in Table 1. In each of these examples, the core of the microparticles obtained was zinc oxide, and the microparticles had a spherical shape. The particle diameters ranged from 500 to 800 nm. Table 2 shows the experimental results in detail.

Example 11

As Example 11, an experiment based on Example 3 was carried out in which the polymer added was changed from PVP to hydroxypropyl cellulose (HPC). The experimental conditions are shown in Table 1. The core of the microparticles obtained was zinc oxide, and the microparticles had a spherical shape. The particle diameter was about 400 nm. Table 2 shows the experimental results in detail.

Comparative Examples 1 and 2

As Comparative Examples 1 and 2, experiments based on Example 1 were carried out involving the addition to DEG of not only PVP and zinc acetate dehydrate, but also 1 mL of water. The experimental conditions are shown in Table 1. The cores of the microparticles obtained were zinc oxide, but some of the microparticles were not spherical in shape. Table 2 shows the experimental results in detail. These results demonstrated that when even a small amount of water is added to DEG to which PVP and zinc acetate dehydrate have been added, it is difficult to obtain only spherical particles.

Comparative Examples 3 and 4

As Comparative Examples 3 and 4, experiments based on Example 1 were carried out in which ethylene glycol (EG) instead of DEG was used as the solvent. Other experimental conditions were also changed; the experimental conditions are shown in Table 1. In Comparative Example 3, the cores of the macroparticles obtained were zinc oxide, but the microparticles were not spherical in shape.

In Comparative Example 4, the core of the microparticles obtained was not composed solely of zinc oxide, but contained also a very small amount of constituents other than oxide. Moreover, the microparticles were not spherical in shape. Table 2 shows the experimental results in detail. These results demonstrated that when EG is used instead of DEG, it is difficult to obtain only spherical particles.

Comparative Example 5

As Comparative Example 5, an experiment based on Example 1 was carried out in which PVP was not added. The experimental conditions are shown in Table 1. The microparticles obtained were zinc oxide, and the microparticles were of spherical shape. However, as was explained in detail in Example 1, the re-dispersibility was poor. These results demonstrated that when PVP is not added, it is difficult to obtain microparticles having a good re-dispersibility.

Comparative Example 6

As Comparative Example 6, an experiment based on Example 2 was carried out in which the refluxing temperature was changed to 140° C. The experimental conditions are shown in Table 1. Only a very small amount of microparticles formed, and the microparticles that were obtained did not have a spherical shape. This demonstrated that when the refluxing temperature is low, it is difficult to obtain microparticles.

Comparative Example 7

As Comparative Example 7, an experiment based on Example 2 was carried out in which PVP was not added. The experimental conditions are shown in Table 1. The microparticles obtained were zinc oxide and the shape of the particles was sometimes spherical, although microparticles that were not spherical were also sometimes obtained. This demonstrated that when PVP is not added, it is sometimes difficult to obtain spherical microparticles.

Comparative Examples 8 to 10

As Comparative Examples 8 to 10, experiments based on Example 9 were carried out in which the concentration of PVP, the concentration of zinc acetate dehydrate or the refluxing time was changed. The experimental conditions are shown in Table 1. In Comparative Examples 8 to 10, the core of the microparticles obtained were zinc oxide, although some or all of the microparticles had shapes that were not spherical. In Comparative Example 8, the concentration of zinc acetate dehydrate was too high. In Comparative Example 9, the PVP concentration was too high. In Comparative Example 10, the refluxing time was too short.

INDUSTRIAL APPLICABILITY

As described in detail above, the present invention relates to core-shell type zinc oxide microparticles, a dispersion containing such microparticles, and a production process and uses of the microparticles and the dispersion. According to this invention, there can be provided core-shell type zinc oxide microparticles having a particle diameter of from about 50 nm to about 1,000 nm, a spherical shape and good dispersibility in water, and there can also be provided a dispersion of such microparticles. The present invention is also able to provide a readily re-dispersible dry powder of core-shell type zinc oxide microparticles, a dispersion of core-shell type zinc oxide microparticles dispersed in a desired dispersion medium, and a high-viscosity dispersion of core-shell type zinc oxide microparticles, that is, a paste of core-shell type zinc oxide microparticles. Moreover, the present invention is able to provide a simple process for producing core-shell type zinc oxide microparticles and dispersions of such zinc oxide microparticles. In this invention, by firing the zinc oxide microparticles and oxidatively removing the polymer, spherical zinc oxide microparticles can be obtained. This invention is useful in that it provides production processes for zinc oxide microparticles and dispersions containing such microparticles which may be employed in, for example, catalysts, antireflection coatings and UV blockers, and it also provides such products.

The invention claimed is:

1. Core-shell type zinc oxide microparticles, wherein the 1) a core portion thereof is a secondary particle formed by a spherical aggregation of primary particles of zinc oxide, 2) the secondary particle is of spherical shape and is not of a non-spherical shape, 3) a polymer layer that forms a shell portion exists on a surface of the secondary particle, wherein the polymer layer is composed of polymer crosslinked between polyvinylpyrrolidone (PVP) and PVP, or polymer crosslinked between hydroxypropyl cellulose (HPC) and HPC, or polymer crosslinked between PVP and HPC, or polymer of PVP or HPC crosslinked between PVP or HPC and polyethylene glycol (PEG), or polymer of PEG crosslinked between PEG and PEG, and 4) the microparticles have an average particle diameter of from 50 nm to 1,000 nm, wherein the microparticles are made by heating and refluxing a mixture comprising a zinc salt hydrate and one or more polymers selected from the group consisting of PVP, HPC, and PEG, in a polyol as a high-boiling-point organic solvent, in the absence of water.

2. The core-shell type zinc oxide microparticles according to claim 1, wherein the polymer layer does not separate from the secondary particle of the core portion even when the microparticles are subjected to rinsing, and is present in a proportion of from 5 wt % to 10 wt %.

3. The core-shell type zinc oxide microparticles according to claim 1, wherein the primary particles have a diameter of from 10 to 20 nm and the secondary particle has a diameter coefficient of variation of 0.1 or less.

4. A core-shell type zinc oxide microparticle powder as a dry powder containing the core-shell type zinc oxide microparticles defined in any one of claims 1 to 3, which has the quality of dispersing in a dispersion medium to which dispersant is not added.

5. A core-shell type zinc oxide microparticle dispersion comprising the core-shell type zinc oxide microparticles defined in any one of claims 1 to 3, which is dispersed in a dispersion medium.

6. The core-shell type zinc oxide microparticle dispersion according to claim 5, wherein the dispersion medium is any one of water, ethanol, terpineol and ethylene glycol, or a mixed solution of a plurality thereof.

7. A cosmetic having an ultraviolet light blocking action, comprising the microparticles, defined in any one of claims 1 to 3.

8. A resin or fiber having an ultraviolet light blocking action, comprising the microparticles defined in any one of claims 1 to 3.

9. A resin or fiber having an ultraviolet light blocking action, comprising the microparticle powder according to claim 4.

10. A resin or fiber having an ultraviolet light blocking action, comprising the microparticle dispersion according to claim 5 or 6.

11. A composition comprising core-shell type zinc oxide microparticles, said microparticles consisting essentially of the core-shell type zinc oxide microparticles according to any one of claims 1 to 3.

12. A process for producing core-shell type zinc oxide microparticles according to claim 1, comprising the steps of:
heating/refluxing a mixture comprising a zinc salt hydrate and a polymer, in a polyol as a high-boiling-point organic solvent, in the absence of water, at a temperature of at least 160° C. so as to cause the zinc oxide microparticles to precipitate and form a core-shell structure.

13. The process for producing zinc oxide microparticles according to claim 12, wherein the zinc salt hydrate is zinc acetate, the polymer is polyvinylpyrrolidone (PVP), hydroxypropyl cellulose (HPC) or polyethylene glycol (PEG), and the polyol is diethylene glycol (DEG).

14. The process for producing zinc oxide microparticles according to claim 12 or 13, wherein the polymer has a concentration (weight of polymer added per unit volume of polyol) of from 100 kg/m$^3$ to 140 kg/m$^3$.

15. The process for producing zinc oxide microparticles according to claim 12 or 13, wherein the polymer has a polyethylene glycol-equivalent average molecular weight of from 4,000 to 5,000.

* * * * *